(12) United States Patent
Colling

(10) Patent No.: US 9,867,583 B1
(45) Date of Patent: Jan. 16, 2018

(54) X-RAY SHIELDING SYSTEM

(71) Applicant: Global Imaging Solutions Company, Farmington Hills, MI (US)

(72) Inventor: Timothy P. Colling, Farmington Hills, MI (US)

(73) Assignee: GLOBAL IMAGING SOLUTIONS COMPANY, Farmington Hills, MI (US)

(*) Notice: Subject to any disclaimer, the term of this patent is extended or adjusted under 35 U.S.C. 154(b) by 0 days.

(21) Appl. No.: 15/427,414

(22) Filed: Feb. 8, 2017

(51) Int. Cl.
*A61B 6/00* (2006.01)
*A61B 6/10* (2006.01)
*G21F 3/00* (2006.01)
*A61B 6/04* (2006.01)

(52) U.S. Cl.
CPC ............... *A61B 6/107* (2013.01); *G21F 3/00* (2013.01); *A61B 6/0407* (2013.01)

(58) Field of Classification Search
CPC .......... A61B 6/107; A61B 6/0407; G21F 3/00
USPC ..................... 250/505.1, 515.1, 517.1, 519.1
See application file for complete search history.

(56) References Cited

U.S. PATENT DOCUMENTS

| 5,099,135 A | 3/1992 | Gemmill |
| 5,417,225 A | 5/1995 | Rubenstein et al. |
| 5,981,964 A | 11/1999 | McAuley et al. |
| 6,448,571 B1 | 9/2002 | Goldstein |
| 6,653,648 B2 | 11/2003 | Goldstein |

FOREIGN PATENT DOCUMENTS

CN 201127616 Y * 10/2008

* cited by examiner

*Primary Examiner* — Michael Maskell
(74) *Attorney, Agent, or Firm* — Brooks Kushman P.C.

(57) ABSTRACT

Disclosed is a shielding system for customized shielding of a patient or an operator from X-rays. The shielding system is mounted on a radiation table with a longitudinal edge. In use, the table is reversibly movable between a first (usually horizontal) orientation and a second (usually vertical orientation). Extending from the radiation table is a post that is associated with a patient handgrip subassembly. The subassembly has a bracket that is securably movable along the longitudinal edge. In the shielding system there are foundational blocks with apertures that receive movable rails from which protective curtains are suspended.

13 Claims, 3 Drawing Sheets

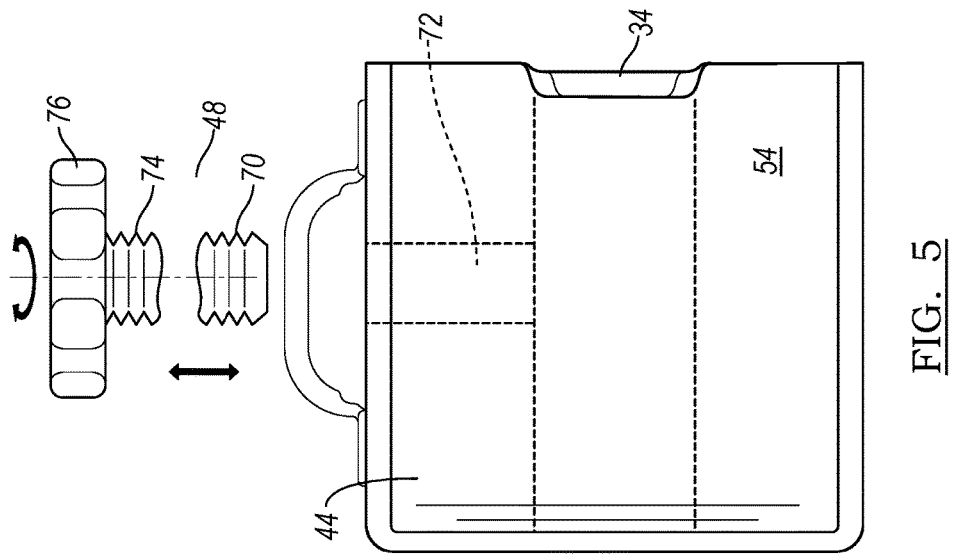
FIG. 5
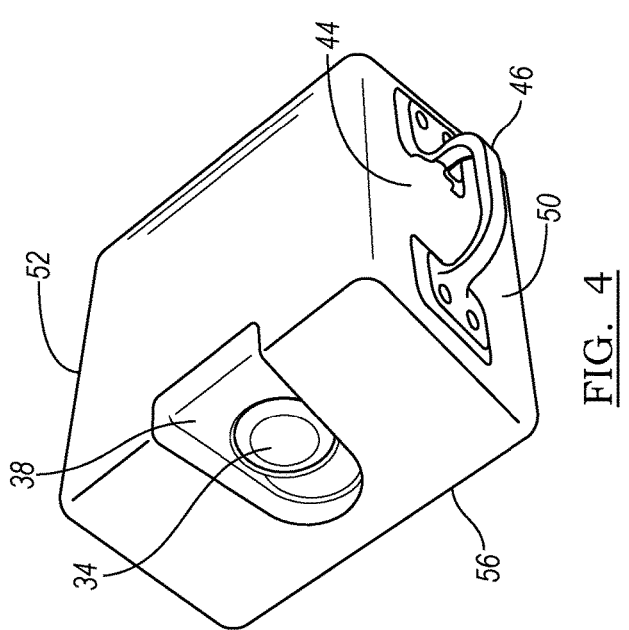
FIG. 4
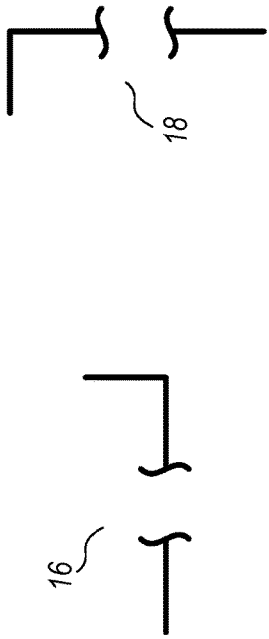
FIG. 6
FIG. 7

X-RAY SHIELDING SYSTEM

TECHNICAL FIELD

This disclosure includes a customizable x-ray shielding system.

BACKGROUND

Among the art considered in preparing this patent application are these references: U.S. Pat. Nos. 5,099,135; 5,417,225; 6,448,571; and 6,653,648.

SUMMARY

Disclosed is a shielding system for customized protection from X-rays. The shielding system is mounted on a patient supporting radiation table with a longitudinal edge. In use, the table is reversibly movable between a first (usually horizontal) orientation and a second (usually vertical) orientation.

Extending orthogonally from the radiation table is a post that is associated with a patient handgrip subassembly. The subassembly has a bracket that is securably movable along the longitudinal edge.

In the shielding system there are foundational blocks. For ease of reference, each block can be considered as having a first (generally horizontal) axis (X-X), a second (generally vertical) axis (Y-Y) and a third (generally lateral) axis (Z-Z).

Facing the radiation table is a bottom surface (A). A post-receiving aperture extends between the bottom surface (A) and an opposing top surface (B). A detent is defined by the bottom surface (A). The detent is configured to be in registration with the bracket. Upon registration, there is little or no movement of the foundational block in relation to the patient handgrip subassembly.

One or more major apertures extend between the bottom surface (A) and the opposing top surface (B). Each major aperture is configured to receive a rail from which for example a lead curtain can be suspended.

Each foundational block has a side surface (C) with means for grasping and locking extending from or defined within the side surface (C). The means for grasping enables an operator to grasp and manipulate the foundational block. The means for locking enables the foundational block to be positioned in relation to the post.

One or more minor apertures extend between the side surface (C) and an opposing side surface (D). Each minor aperture is configured to receive a rail if desired.

Each foundational block has an operator-facing side and a patient-facing side.

The rail has a proximal section that is received by a major aperture or a minor aperture depending on table orientation. Extending from the proximal section is a distal section. In use, a rail can be turned within an associated aperture. Regardless of radiation table orientation, one or more radio-opaque curtains can be suspended in a desired position from the distal section.

BRIEF DESCRIPTION OF THE DRAWINGS

FIG. 4 is a quartering perspective view from below looking upwardly at the foundational block;

FIG. 5 shows a side view of the block as seen by an operator with a side (C) uppermost;

FIG. 6 schematically depicts a first orientation of the radiation table; and

FIG. 7 schematically depicts a second orientation of the radiation table.

DETAILED DESCRIPTION

Figure 1:
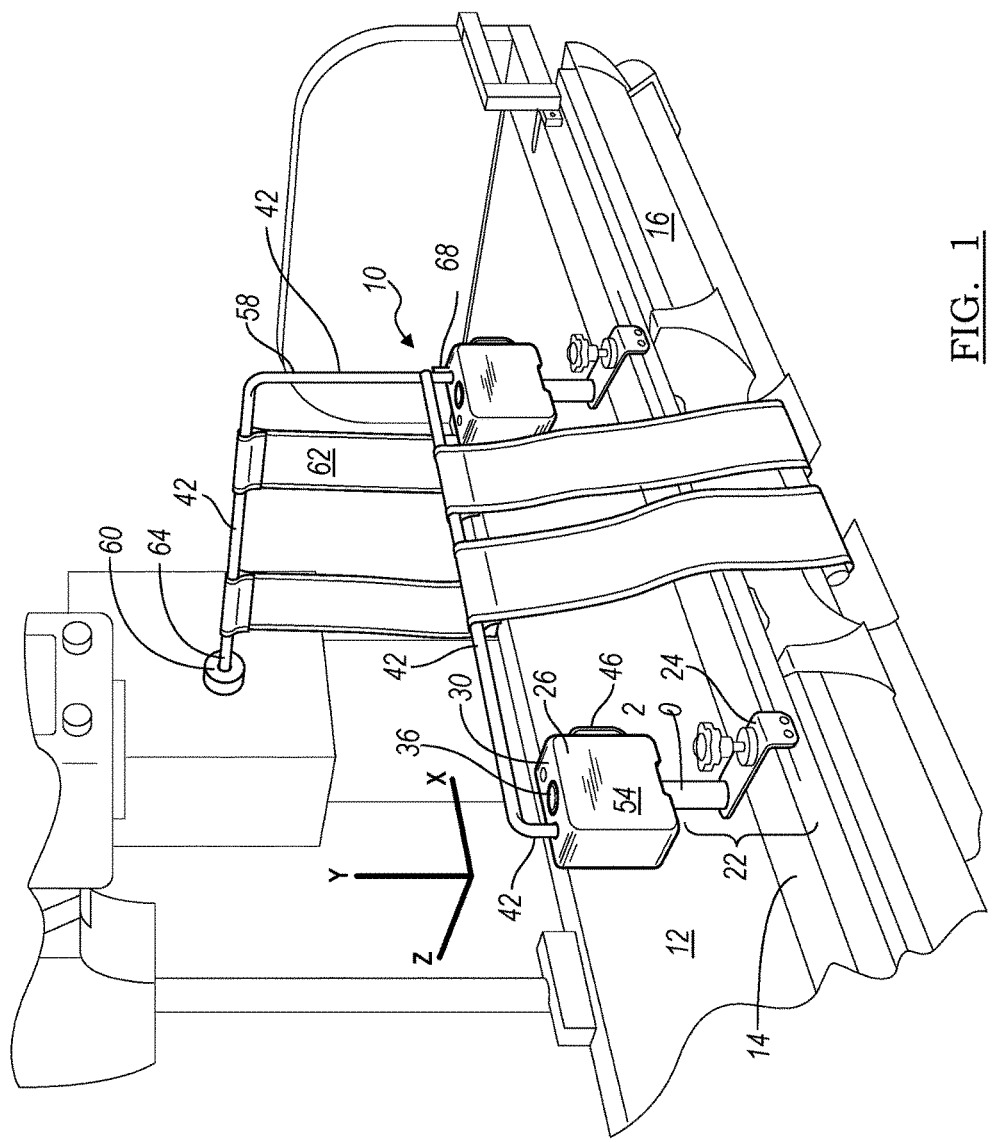
FIG. 1 is a quartering perspective view of a typical environment in which a shielding system is deployed.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Disclosed is a shielding system 10 for use in alternative configurations as customized shielding from X-rays. The shielding system 10 is mounted on a radiation table 12 with a longitudinal edge 14. In use, the table 12 is reversibly movable between a first (usually horizontal) orientation 16 and a second (usually vertical) orientation 18. The table 12 has a surface that supports a patient.

Extending from the radiation table 12 is a post 20 that is associated with a patient handgrip subassembly 22. The subassembly 22 has a bracket 24 that is securably movable along the longitudinal edge 14.

In the shielding system 10 there are one or more foundational blocks 26. For ease of reference, each block can be considered as having a first (generally horizontal) axis (X-X), a second (generally vertical) axis (Y-Y) and a third (generally lateral) axis (Z-Z) (see, e.g. FIG. 1).

Figure 3:
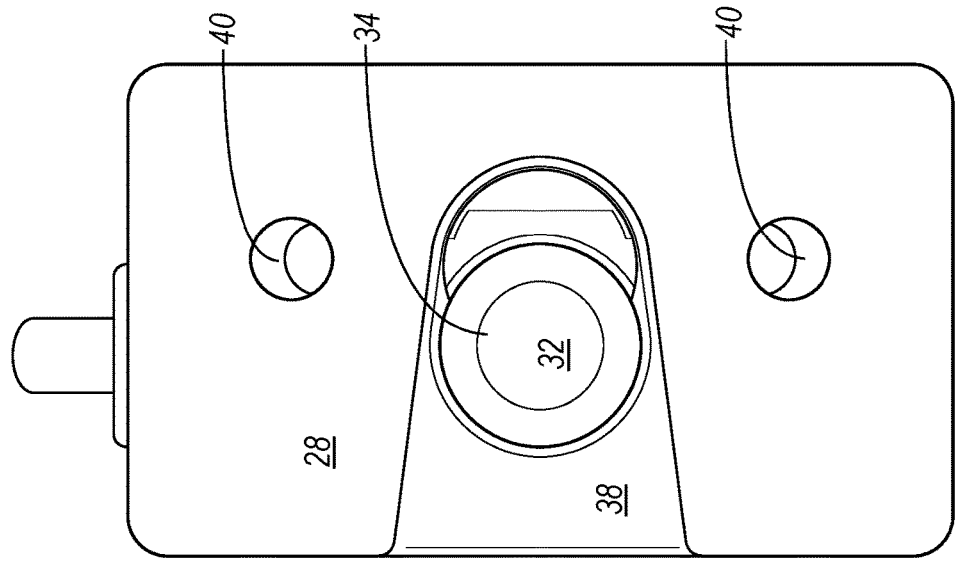
FIG. 3 depicts a representative bottom surface (A) of the foundational block.
Figure 2:
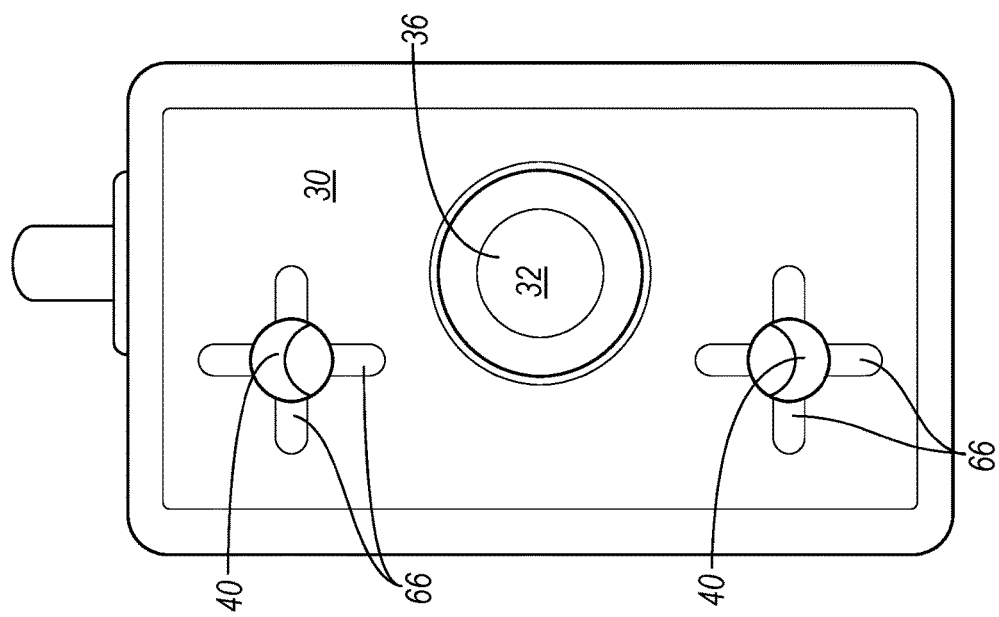
FIG. 2 depicts a representative top surface (B) of a foundational block that forms a part of the shielding system.

Facing the radiation table 12 is a bottom surface (A) 28. A post-receiving aperture 32 extends between the bottom surface (A) 28 (FIG. 3) and an opposing top surface (B) 30 (FIG. 2). A detent 38 is defined within the bottom surface (A). The detent 38 is configured to be in registration with the bracket 24. Preferably the detent has edges that diverge (FIG. 3). Divergence allows the foundational block 26 to be suitably engaged by the bracket 24. Upon registration, there is little or no movement of the foundational block 26 in relation to the patient handgrip subassembly 22.

One or more major apertures 40 extend between the bottom surface (A) 28 and the opposing top surface (B) 30. Each major aperture is configured to receive a rail 42.

Each foundational block 26 has a side surface (C) 44 (FIG. 4) with means for grasping 46 extending from the side surface (C) 44 and means for locking 48 (FIG. 5). The means for grasping 46 includes a handle (as shown) or a partially recessed cup pull or draw handle or flush ring pull handle. The means for grasping 46 enables an operator to grasp the foundational block 26. The means for locking 48 (FIG. 5) enables the foundational block 26 to be securably positioned in relation to the post 20.

One or more minor apertures 50 extend at least partially between the side surface (C) 44 and an opposing side surface (D) 52. Each minor aperture 50 is configured to receive a rail 42 if desired.

Each foundational block 26 has an operator-facing side 54 and a patient-facing side 56.

The rail 42 has a proximal section 58 (FIG. 1) that is received by a major aperture 40 or a minor aperture 50. Extending from the proximal section 58 is a distal section 60. Regardless of radiation table orientation, one or more radio-opaque curtains 62 can be hung from the distal section 60 to allow flexibility in adapting to operator and patient examination requirements. It will be appreciated that the curtains 62 are preferably formed from an x-ray absorbing material. Such curtains 62 may for example be 20" long×26" wide. But the curtains 62 can be of any length and width. Further, the curtains 62 may have any desired x-ray attenuation characteristics.

In one embodiment there is a knob 64 that is received at an end of the distal section 60 of the rail 42 for constraining lateral movement of the one or more radio-opaque curtains 62 along the distal section 60 of the rail 42.

Preferably the major apertures 40 terminate at the opposing top surface (B) 30 (FIG. 2) and slots 66 extend radially from the major apertures 40. The slots 66 are configured to engage lugs 68 that extend radially from the proximal section 58 of the rail 42 to preclude a twisting motion of the rail 42 when seated within an associated aperture. This feature influences rail 42 positioning regardless of table orientation.

It will be appreciated that the first table orientation 16 is generally horizontal (FIG. 6). orientation, so that the first axis (X-X) is horizontal, the second axis (Y-Y) is vertical and the third axis (Z-Z) is lateral.

In some situations, the radiation table is turned to or towards the orientation shown in FIG. 7. For reference, the first orientation is generally vertical. In that case, the first axis (X-X) is vertical, the second axis (Y-Y) is horizontal and the third axis (Z-Z) is lateral. It will be appreciated that the orientation of FIG. 7 could be inverted.

In most uses, the rail 42 can be twisted within the major aperture 40 or minor aperture 50 so that the distal section 60 of the rail 42 extends horizontally regardless of table orientation. After reaching a desired rail orientation, an interference fit between the rail 42 and the associated aperture secures the rail 42 in position regardless of table orientation.

Alternatively, the rail position is secured by engaging a lug 68 within a slot 66. It will be appreciated that the distal section 60 of the rail 42 may be positioned so that the distal section 60 extends horizontally across the table 12. Optionally, if desired, the distal section 60 may lie in parallel with the longitudinal edge 14 of the table 12.

Preferably, there are two foundational blocks 26 for optimized shielding of the patient and operator from radiation. Each block 26 supports a rail 42. One rail 42 has a distal section 60 that extends horizontally across the table. The other rail 42 has a distal section 60 that lies in parallel with the longitudinal edge 14 of the table.

To secure a foundational block 26 in relation to an associated anchoring post 20, means for locking 48 (FIG. 5) are provided. Such locking means 48 include for example a threaded bolt having a lower end portion 70 that is received by a threaded through-hole 72 that extends from the side surface (C) 44 to the post-receiving aperture 32 and an upper end portion 74 that terminates in an end member 76 (such as a knurled knob) that can be gripped by a hand.

In some cases, the first table orientation 16 lies between plus and minus 30 degrees from a horizontal axis. In others, when the radiation table is positioned upright, the first table orientation 16 lies between plus and minus 180 degrees from a vertical axis.

Although the foundation blocks are depicted as generally cubical, it will be appreciated that such blocks may be shaped in various geometries and sizes, and have non-parallel faces that may or may not be planar.

TABLE OF REFERENCE NUMERALS 10 shielding system
12 radiation table
14 longitudinal edge
16 first orientation
18 second orientation
20 post
22 handgrip subassembly
24 bracket
26 foundational blocks
28 bottom surface (A)
30 top surface (B)
32 post-receiving aperture
34 entrance region
36 exit region
38 detent
40 major apertures
42 rail
44 side surface (C)
46 means for grasping
48 locking
50 minor apertures
52 side surface (D)
54 operator-facing side (E)
56 patient-facing side (F)
58 proximal section of rail αdistal section of rail
62 opaque curtains
64 knob
66 slots
68 lugs
70 lower end portion
72 through-hole
74 upper end portion
76 end member While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A shielding system for customized shielding from X-rays with a patient-supporting radiation table having a longitudinal edge, the patient-supporting radiation table being reversibly movable between a first orientation and a second orientation, the shielding system extending from a post associated with a patient handgrip subassembly having a bracket, the patient handgrip subassembly being movable and securable along the longitudinal edge, the shielding system comprising one or more foundational blocks, each block having a first axis (X-X), a second axis (Y-Y) and a third axis (Z-Z) and a bottom surface (A) that faces the patient-supporting radiation table and an opposing top surface (B);

a post-receiving aperture that extends at least partially between the bottom surface (A) and the opposing top surface (B), the post-receiving aperture having an entrance region and an exit region;

a detent defined by the bottom surface (A), the detent being configured to be in registration with the bracket so that upon registration, there is little or no movement of the foundational block in relation to the patient handgrip subassembly;

one or more major apertures that extend at least partially between the bottom surface (A) and the opposing top surface (B), each major aperture being configured to receive a rail;

a side surface (C) with means for grasping and means for locking, the means for grasping enabling an operator to grasp the foundational block and the means for locking enabling the foundational block to be positioned in relation to the post;

one or more minor apertures that extend at least partially between the side surface (C) and an opposing side surface (D), each minor aperture being configured to receive a rail;

an operator-facing side; and a patient-facing side, the rail having a proximal section that is received by a major aperture or a minor aperture and a distal section that extends from the proximal section so that one or more radio-opaque curtains can be suspended from the distal section.

2. The shielding system of claim 1, further including:
a knob that is received at an end of the distal section of the rail for constraining lateral movement of the one or more radio-opaque curtains along the distal section of the rail.

3. The shielding system of claim 1, wherein the major apertures terminate at the opposing top surface (B) and slots extend radially from the major apertures, the slots being configured to engage lugs that extend radially from the proximal section of the rail to preclude a twisting motion of the rail within an associated aperture when the proximal section is seated, thereby influencing rail positioning regardless of table orientation.

4. The shielding system of claim 1, wherein the first orientation is a generally horizontal orientation.

5. The shielding system of claim 1, wherein the first orientation is a generally vertical orientation.

6. The shielding system of claim 1, wherein the rail can be twisted within the major aperture or minor aperture so that the distal section of the rail extends horizontally regardless of table orientation.

7. The shielding system of claim 1, wherein there are two foundational blocks, each supporting a rail, one rail having a distal section extending horizontally across the patient-supporting table, and the other rail having a distal section that lies in parallel with the longitudinal edge of the patient-supporting radiation table.

8. The shielding system of claim 1, wherein the means for locking includes a threaded bolt having a lower end portion that is received by a threaded through-hole that extends from the side surface (C) to the post-receiving aperture and an upper end portion that terminates in an end member that can be gripped by a hand.

9. The shielding system of claim 4, wherein the first axis (X-X) is horizontal, the second axis (Y-Y) is vertical and the third axis (Z-Z) is lateral.

10. The shielding system of claim 4, wherein the first patient-supporting radiation table orientation lies between plus and minus 30 degrees from a horizontal axis.

11. The shielding system of claim 5, wherein the first axis (X-X) is vertical, the second axis (Y-Y) is horizontal and the third axis (Z-Z) is lateral.

12. The shielding system of claim 5, wherein the first patient-supporting radiation table orientation lies between plus and minus 180 degrees from a vertical axis.

13. The shielding system of claim 6, wherein the distal section of the rail extends horizontally across the patient-supporting radiation table or in parallel with the longitudinal edge of the patient-supporting radiation table.

* * * * *